United States Patent [19]

Thomas et al.

[11] Patent Number: 5,215,080
[45] Date of Patent: Jun. 1, 1993

[54] ATTACHABLE INSULATING ICING SYSTEM

[75] Inventors: James E. Thomas, 68 Greenridge Ct., Lake Oswego, Oreg. 97034; Andrew Gordon, Portland, Oreg.

[73] Assignee: James E. Thomas, Lake Oswego, Oreg.

[21] Appl. No.: 558,220

[22] Filed: Jul. 26, 1990

[51] Int. Cl.⁵ .................................................. A61F 7/02
[52] U.S. Cl. ...................................... 128/402; 128/380
[58] Field of Search ............... 128/401, 403, 379, 380; 62/259, 3, 530

[56] References Cited

U.S. PATENT DOCUMENTS

| | | | |
|---|---|---|---|
| 3,491,761 | 1/1970 | Baker | 128/402 |
| 3,882,873 | 5/1975 | Arango | 128/402 |
| 3,889,684 | 6/1975 | Lebold | 128/402 |
| 4,055,188 | 10/1977 | Pelton | 128/402 |
| 4,344,303 | 8/1982 | Kelly, Jr. | 128/402 |
| 4,527,566 | 7/1985 | Abare | 128/402 |
| 4,576,169 | 3/1986 | Williams | 62/530 |
| 4,628,932 | 12/1986 | Tampa | 128/402 |
| 4,676,247 | 6/1987 | Van Cleve | 128/402 |
| 4,753,240 | 6/1988 | Sparks | 128/379 |
| 4,886,063 | 12/1989 | Crews | 62/530 |
| 4,899,749 | 2/1990 | Laroco | 128/402 |
| 5,016,629 | 5/1991 | Kanare | 128/402 |

OTHER PUBLICATIONS

Advertising and Instruction materials on Thermosport (TM), from Omniplex, Inc., dated 1989.
Advertising brochures and related materials for Dura*-Kold, undated.

Primary Examiner—Mark S. Graham
Attorney, Agent, or Firm—Dellett, Smith-Hill and Bedell

[57] ABSTRACT

An icing system is disclosed that has an insulating layer of wetsuit rubber, with a nylon pouch sewn onto it. The nylon pouch is divided, depending on configuration, into two or three compartments by hook and loop fasteners that are used in strips to both close the flap of the pouch and divide it into the compartments as desired. The compartments are designed to hold standard sizes of resealable sandwich and freezer bags half filled with ice. The multiple compartments allow varying amounts of ice to be put around different areas of the same body part, make it flexible, and permit a maximum of mobility on the part of the user. The wetsuit rubber that is used as an outer insulator allows this icing system to use ice with maximum efficiency, and yet makes the system flexible, light weight, non-leaking and non-irritating, permitting maximum mobility on the part of the user. Flanges of the wetsuit rubber material contact the wearer and prevent warm air in the environment from lowering the efficiency of ice utilization.

4 Claims, 3 Drawing Sheets

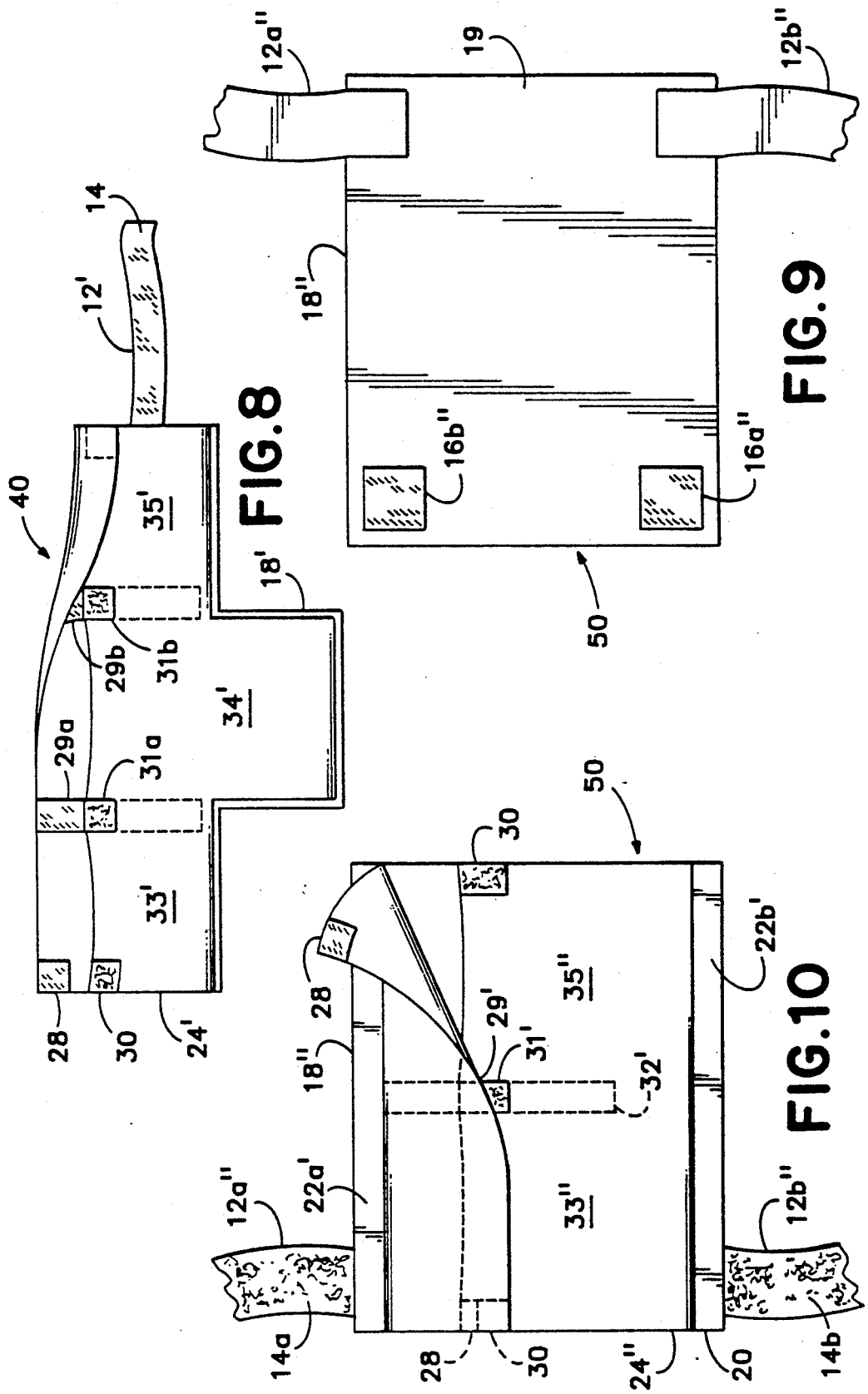

ATTACHABLE INSULATING ICING SYSTEM

BACKGROUND OF THE INVENTION

This invention relates to the field of devices used in the application of heat or cold to parts of the human body, and more particularly to the field of insulating icing systems attachable to the joints of various appendages of a human or animal body.

There are presently known a large number of devices used to apply heat or cold to parts of the human body. One set of such prior art devices relies on hot or cold water to supply the therapeutic source of heat or cold. While liquid water at different temperatures is generally conveniently available, the heat or cold carrying capacity of water is limited when no phase change is involved.

Another set of such prior art devices relies on gel packs as a source of heat or cold. While some such packs have more heat or cold carrying capacity than water, they are relatively expensive and their capacity is still limited. U.S. Pat. No. 4,899,749 discloses thermal vascular dilating device and method employing a cylindrically shaped water-tight container with a threaded spout and cap opening for filling the container. Hook and loop fastener straps are used to secure the device to the arm of the human body.

For applying cold to (removing heat from) the human body, ice has long been recognized as having superior cold carrying capacity when compared with all simple liquids and many other substances that are capable of undergoing a phase change. The phase change energy of ice turning to water is very high, and ice is therefore a very effective source of cold. Ice is also inexpensive and readily available in a variety of settings.

U.S. Pat. No. 4,753,240 discloses a device for immobilizing and applying heat or cold to a body part. It includes one or more pouches for enclosing ice packs or heat packs. A complex arrangement of straps allows these packs to be positioned in various relationships to an arm and shoulder. This device assumes that a certain degree of immobility is desirable or necessary, and, accordingly, includes metal stays for this purpose. However, on many occasions, people with minor body part injuries wish to remain as active as possible, while still deriving the beneficial effects of cold therapy, and this device is inappropriate to their needs.

U.S. Pat. No. 4,628,932 discloses an ice pack specialized for use on the human knee. It includes multiple compartments for receiving the ice and a hole intended to be aligned with the patella to keep it from being subjected to the cooling effect of the ice. The multiple compartments are accessed through a zipper and the pack is secured to the leg with a pattern of hook and loop fastener strips. This pack is highly specialized for the knee and is fastened in a way that presumes some immobility on the part of user. Moreover, zippers are expensive and tend to be unreliable with extended use in a moist environment.

What is desired is an icing system that can be applied to a variety of body parts, that uses ice with maximum efficiency, that allows varying amounts of ice to be put around different areas of the same body part, that is easily attached and detached, that is flexible, light weight, and non-irritating, that permits a maximum of mobility on the part of the user, that permits the ice container to be readily exchanged or reloaded very easily, that utilizes an ice container that is cheap, disposable, non-leaking and readily available, and that is simple and utilizes common materials, so that manufacturing costs and selling price can be minimized.

It is an object of the present invention to provide a system for applying therapeutic cold to an injured body part that utilizes ice as its source of cold.

It is also an object of the present invention to provide an icing system that can be used in different configurations with a variety of different places on different appendages of a human or animal body.

It is also an object of the present invention to provide an icing system that uses its ice with a maximum of efficiency, by providing for very effective insulation from the ambient environment so that as much cold as possible is communicated to the desired area around the body part with a minimum of wasteful dissipation into the ambient environment.

It is also an object of the present invention to provide an icing system that allows differing amounts of ice to be applied to various regions around one injured body part, depending on the nature of the injury.

It is also an object of the present invention to provide an icing system that is easily and simply attachable and detachable.

It is also an object of the present invention to provide an icing system that is flexible, light weight, non-leaking and non-irritating.

It is also an object of the present invention to provide an icing system that permits a maximum of mobility on the part of the user.

It is also an object of the present invention to provide an icing system that permits the ice container to be readily exchanged or reloaded very easily.

It is also an object of the present invention to provide an icing system that utilizes an ice container that is cheap, disposable, and readily available.

It is also an object of the present invention to provide an icing system that is simple and utilizes common materials, so that manufacturing costs and selling price can be minimized.

SUMMARY OF THE INVENTION

Accordingly, the present invention is an icing system that can be applied to a variety of body parts, that uses ice with maximum efficiency, that allows varying amounts of ice to be put around different areas of the same body part, that is easily attached and detached, that is flexible, light weight, non-leaking and non-irritating, that permits a maximum of mobility on the part of the user, that permits the ice container, or other source of cold, to be readily exchanged or reloaded very easily, that utilizes an ice container that is cheap, disposable, non-leaking, and readily available, and that is simple and utilizes common materials, so that manufacturing costs and selling price can be minimized.

The icing system of the present invention has multiple compartments, an insulating layer of wetsuit rubber, including flanges, hook and loop straps, fasteners, and dividers in a unique geometry, and is designed to use resealable plastic sandwich and freezer bags as its ice containers. The multiple compartments allow varying amounts of ice to be put around different areas of the same body part, make it flexible, and permit a maximum of mobility on the part of the user. The wetsuit rubber that is used as an outer insulator and in the flanges that adjoin the user's skin allow this icing system to use ice with maximum efficiency, and yet make the system flexible, light weight, non-leaking and non-irritating, permitting maximum mobility on the part of the user. The hook and loop fastener straps are in unique configurations in some models, allowing them to be applied to a variety of body parts and also permitting them to be easily attached and detached. The use of hook and loop fasteners to separate the multiple compartments makes it possible to combine the compartments as desired. The use of hook and loop fasteners to open and close the compartments facilitates easy exchange or reloading of ice containers. And, the use of resealable plastic type sandwich and freezer bags as ice containers means that these ice containers are cheap, disposable, non-leaking, readily available, and easy to exchange. Furthermore, the icing system of the present invention is simple and utilizes common materials, so that manufacturing costs and selling price can be minimized.

BRIEF DESCRIPTION OF THE DRAWINGS

FIG. 8 is a view of the inside surface of the second configuration of the icing system of the present invention, FIG. 9 is a view of the outside surface of the third configuration of the icing system of the present invention, and FIG. 10 is a view of the inside surface of the third configuration of the icing system of the present invention.

DETAILED DESCRIPTION

Figure 1:
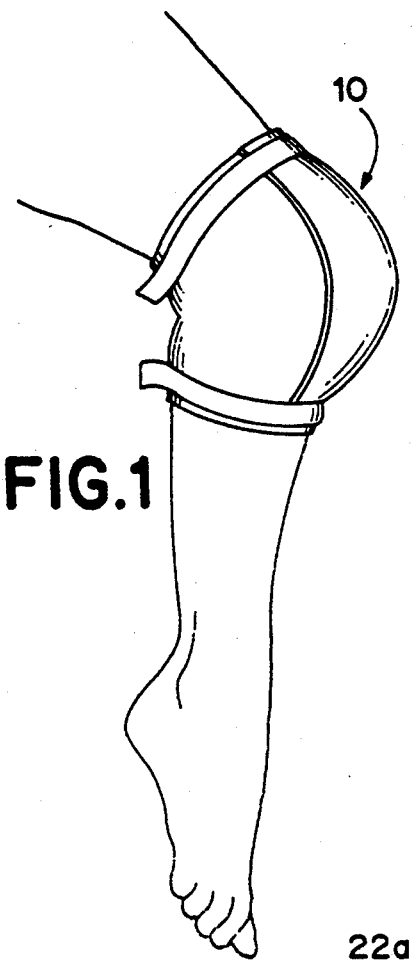
FIG. 1 shows a first configuration of the icing system of the present invention attached to a knee joint.
Figure 2:
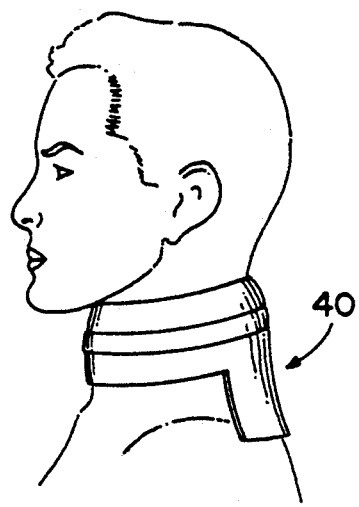
FIG. 2 shows a second configuration of the icing system of the present invention attached to a neck.
Figure 3:
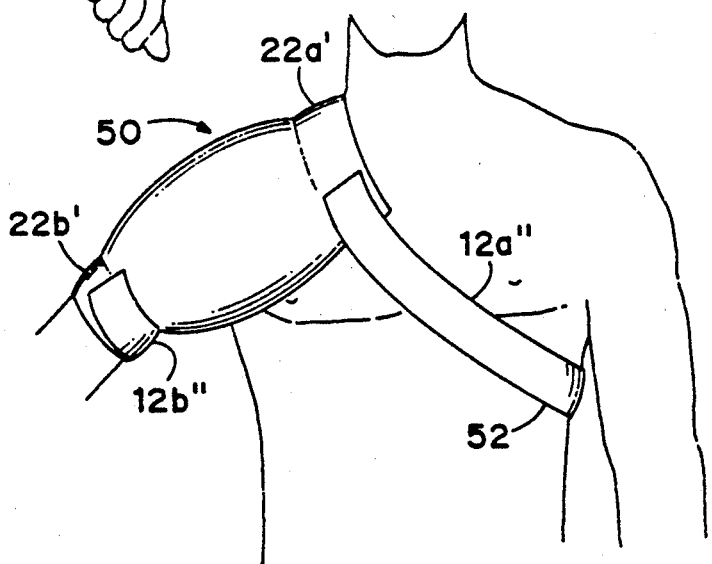
FIG. 3 shows a third configuration of the icing system of the present invention attached to a shoulder.

Referring to FIG. 1, the first configuration 10 of the icing system of the present invention is shown attached to a knee. This configuration 10 is also suitable for use with elbows. To accommodate individuals of differing sizes and different parts of the human body, this configuration 10 is made in several sizes, each of which is compatible with a commonly available resealable plastic sandwich or freezer bag. FIG. 2 shows the second configuration 40 of the icing system of the present invention attached to a neck. FIG. 3 shows the third configuration 50 of the icing system of the present invention attached to a shoulder.

Figure 4:
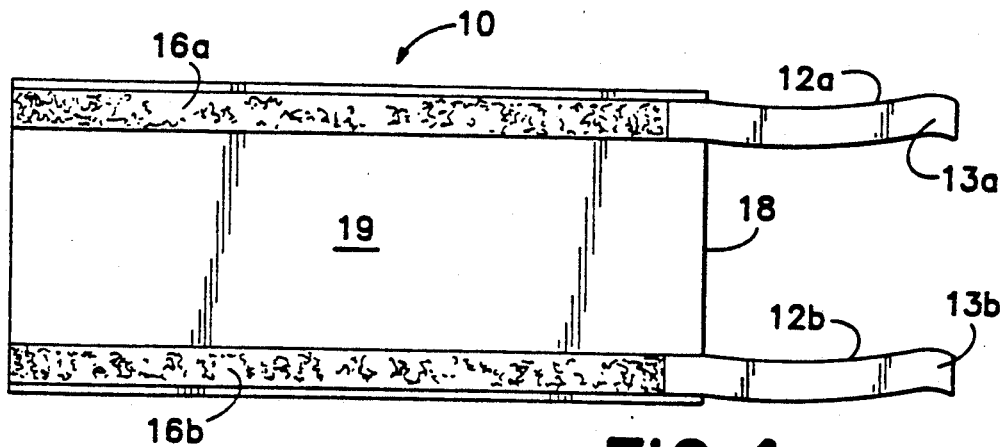
FIG. 4 is a view of the outside surface of the first configuration of the icing system of the present invention.

Referring now to FIG. 4, the outer side of the first configuration 10 of the icing system of the present invention is shown. An insulating layer 18 of polychloroprene wetsuit rubber about an ⅛ inch thick (approximately 3.2 cm) has two strips 16a and 16b of hook and loop fastener loop material affixed to it, loop side out. The sheet of wetsuit rubber also has two straps 12a and 12b affixed to it at one end of the strips 16a and 16b.

These straps 12a and 12b are hook and loop fastener hook material, but the side of them shown in this view is the backing side of the hook material, not the hook side. Stitching is used to accomplish the affixing, but other methods, such as adhesives, could be used. The strips, 16a and 16b, and straps, 12a and 12b, are affixed to the textured side 19 of the insulating layer 18 of wetsuit rubber.

Wetsuit rubber has a textured side and a smooth side. The smooth side of wetsuit rubber is actually rubber, while the textured side is covered with a thin nylon layer. Internally, wetsuit rubber is composed of a large number of very small compartments that are not interconnected. Thus, it is waterproof throughout and a very high quality thermal insulator.

Figure 5:
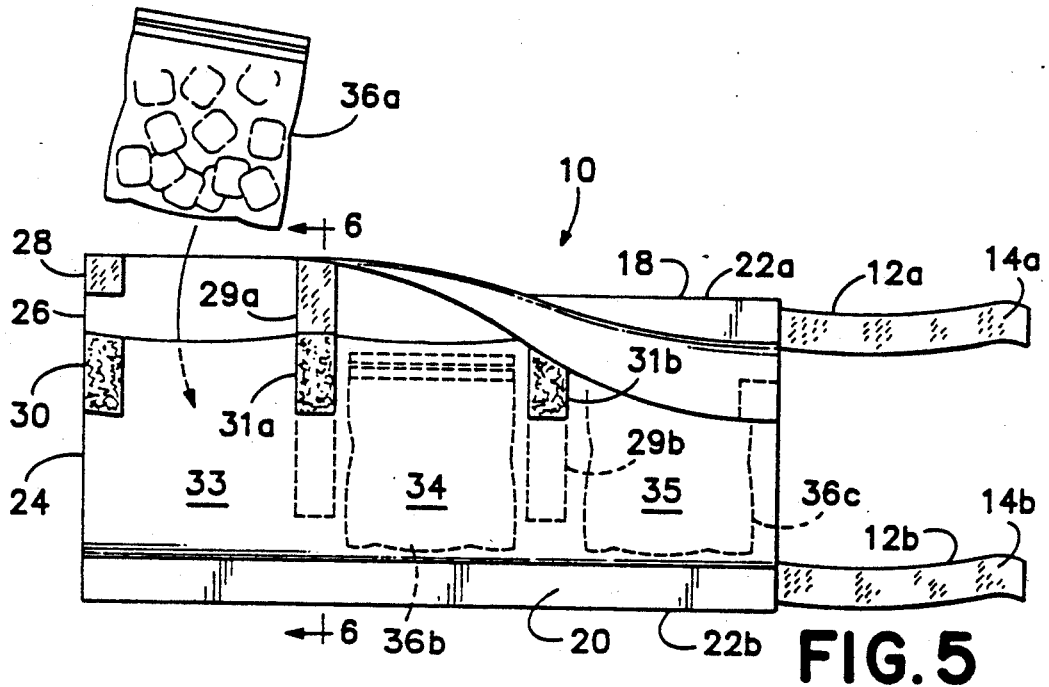
FIG. 5 is a view of the inside surface of the first configuration of the icing system of the present invention.

Referring now to FIG. 5, the inner side of the first configuration 10 of the icing system of the present invention is shown. From this view, the hook sides 14a and 14b of straps 12a and 12b are visible. The smooth side 20 of the insulating layer 18 is also presented in this view. A nylon pouch 24 is affixed to the smooth side 20 of insulating layer 18 and extends along its length. However, the nylon pouch 24 does not extend to either the top or bottom of insulating layer 18, leaving two flange portions 22a and 22b of the smooth side 20 exposed. These flange portions 22a and 22b are located in the same region of the insulating layer 18 as the straps 12a and 12b and strips 16a and 16b, but on the smooth side 20 of the insulating layer. This arrangement of the flange portions 22 and the straps 12 and strips 16 allows the insulating layer 18 to be in place in firm insulating contact with the patient's body.

Figure 6:
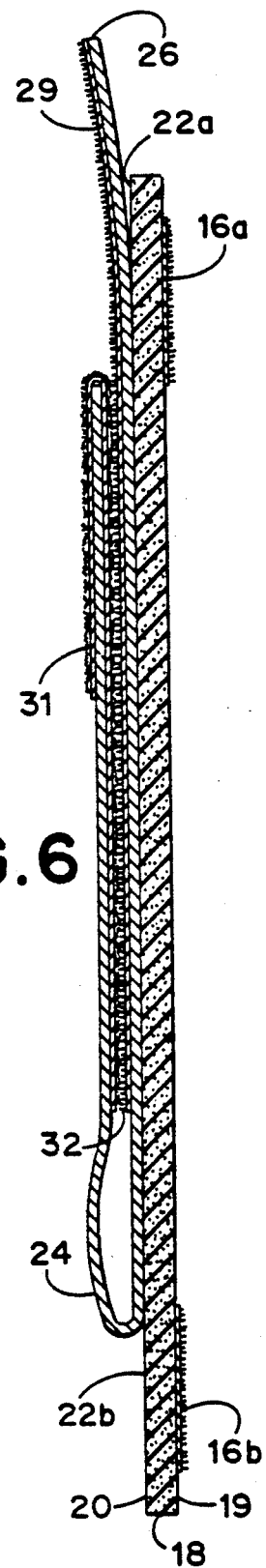
FIG. 6 is a cross sectional view of the first configuration of the icing system of the present invention.

The nylon pouch 24 has a cover 26 that is closed by pairs of hook and loop fasteners 28 and 30, and 29 and 31, as well as their counterparts at the other end (not fully visible). Referring now to FIG. 6, a cross sectional view of the first configuration 10 of the icing system of the present invention, along with FIG. 5, note that the hook and loop fastener pair 29 and 31 shown in FIG. 5 extend deep into the nylon pouch 24 to point 32, thereby serving, along with their counterpart at the other end 29b and 31b (not fully visible in FIG. 5) to divide the nylon pouch 24 into three compartments 33, 34, 35, when the fasteners are fastened. Each compartment of all of the configurations is designed to hold a standard size resealable plastic sandwich or freezer bag 36. Ice is put into these resealable plastic bags 36, which are then placed in one or more of the compartments 33, 34, 35 depending on the nature of the injury being treated and where cold is desired.

The ability to divide or not divide the nylon pouch 24 into compartments 33, 34, 35, provided by the extended hook and loop fastener pairs 29a, 31a and 29b, 31b, permits a user to arrange the resealable plastic sandwich and freezer bags 36 into a novel arrangement adapted to his particular circumstances, putting the ice containing bags in non-standard locations if such is his desire. For instance, by closing off one compartment and not putting any ice in it, and using some inert stuffing material to position one resealable plastic bag containing ice, that bag can located at any intermediate position across the region that is normally used as a compartment divider.

The first configuration has been made in a variety of sizes to accommodate the elbows and knees of a wide range of individuals or types of animals. An extra large version has compartments 33, 34 and 35 that are 7"×8", 7"×9.5", and 7"×8", respectively. A large version has compartments 33, 34 and 35 that are all 7"×7". Both of these versions are for use with quart capacity resealable bags. The medium size version has compartments 33, 34 and 35 that are 5.5"×5", 5.5"×5.5", and 5.5"×5", respectively. The small version only has two compartments that are both 6"×4". Both the medium and small versions are for use with sandwich size resealable bags.

To use the icing system of the present invention, fill a resealable plastic bag of the appropriate size half full of ice and seal the bag, eliminating as much air as possible in the process. Seal by applying even pressure in one continuous motion, moving from one edge to the other, while the bag is lying on a table or counter with the contents hanging over the edge. Since not all resealable bags are reliably water tight, it may be necessary to double-bag the ice to ensure 100% dryness. If two bags are used, place the sealed end of the first bag into the second bag first. And, be sure to remove as much air as possible from both bags to minimize unwanted insulating effects of the air. Place the desired number of bags in the compartments that are appropriate to the nature of the injury. For the first configuration 10 of the icing system, fasten the icing system loosely into a circle and then place the arm or leg through it. Once the icing system is in a suitable position, adjust the straps for a better fit. Straps 12a and 12b wrap around the patient and the icing system and their hook sides 14a and 14b mate with the loop material of strips 16a and 16b.

Figure 7:
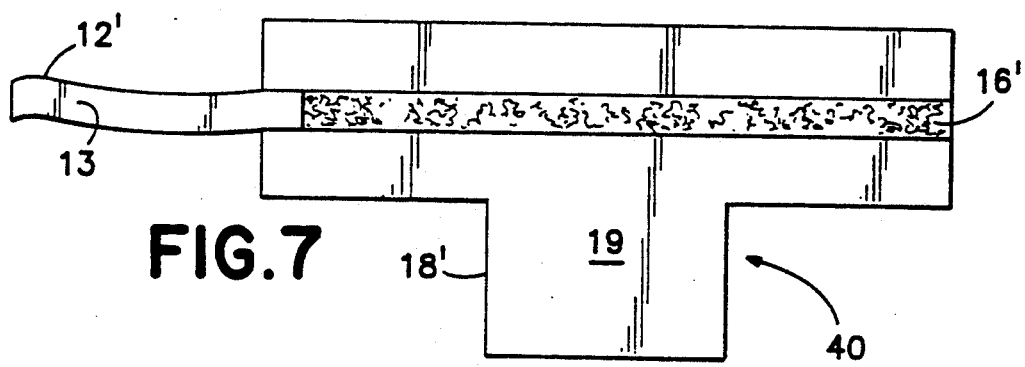
FIG. 7 is a view of the outside surface of the second configuration of the icing system of the present invention.

Referring now to FIGS. 7 and 8, the second configuration 40 of the icing system of the present invention, the one designed for use around a neck, is similar to the first configuration 10 with the following exceptions. The insulating layer 18' has a different shape that can be described as a small, almost square rectangle centered on the lower side of a long rectangle. Instead of two mating straps 12a and 12b and strips 16a and 16b, as in the first configuration, the second configuration 40 has one mating strap 12', and strip 16' is affixed to the textured side 19 of insulating layer 18' halfway down the short dimension of the long rectangle. The compartments 33' and 35' on each end are smaller, 6"×4", while the compartment 34' in the middle is larger, 6.5"×8". The smaller compartments 33' and 35' use sandwich size resealable bags 36, while the larger compartment 36' uses quart size resealable bags 36. This configuration 40 also does not have flange portions 22a and 22b in the insulating layer 18, as did the first configuration 10. Other than these differences, it is very similar to the first configuration 10.

The second configuration 40 is used for necks. The extended central compartment 34' usually hangs down the back of the neck, while the two side compartments 33' and 34' wrap around the side of the neck. Alternatively, the second configuration 40 can be used to ice the upper neck and back of the head, by attaching the icing system with the extended compartment 34' oriented upwardly. When this orientation is used, the long compartment is secured to the head using a readily available athletic headband (not shown).

The third configuration 50 of the icing system of the present invention, the one which is adapted for use in treating shoulders, is shown in FIGS. 9 and 10. The insulating layer 18 is a 12" by 15' rectangle in this configuration 50. The hook and loop hook straps 12a" and 12b" are disposed at one end of the longest dimension, while the mating strips 16a" and 16b" of loop material are at the other. Referring to FIG. 3, this arrangement of strips 16" and straps 12", each 2" wide, permits the third configuration 50 to be worn around the chest 52. Strap 12a" is circled around the arm before it connects to mating strip 16a" (not visible). Strap 12b" wraps around the chest under the arm 52 before mating with strip 16b" (not visible). Flange portions 22a' and 22b' of the insulating layer 18" are thus brought into contact with the wearer's skin or clothing to maximize ice utilization efficiency.

As in the first configuration 10 and the second configuration 40, the third configuration 50 has a nylon pouch 24" sewn onto the smooth surface 20 of insulating layer 18 of wetsuit rubber. In the third configuration 50, the nylon pouch 24' is divided into only two compartments 33" and 35" by the single pair of hook and loop fasteners 29' and 31'. Usually, however, the compartments 33" and 35" will not be separated, but use one large 14"×10" compartment accommodating a gallon size resealable bag 36. As was shown in FIG. 6 for the first configuration, this pair of hook and loop fasteners 29' and 30' extends into the pouch all the way to point 32', effectively dividing the nylon pouch 24" into the two compartments 33" and 35". The flap of the nylon pouch 24" is secured with three pairs of hook and loop fasteners, one pair at each end 28 and 30, and one extended pair in the center 29' and 31'.

While a preferred embodiment of the present invention has been shown and described, it will be apparent to those skilled in the art that many changes and modifications may be made without departing from the invention in its broader aspects. The claims that follow are therefore intended to cover all such changes and modifications as fall within the true spirit and scope of the invention.

We claim:

1. An attachable insulating icing system comprising:
   an insulating layer;
   hook and loop fastener straps and strips affixed to an outer surface of the insulating layer;
   a pouch affixed to an inner surface of the insulating layer, the pouch being separated into a plurality of compartments by hook and loop fasteners extending over a substantial portion of the length of one dimension of the pouch; and
   removable ice containers placed within the pouch.

2. An attachable insulating icing system as recited in claim 1 wherein the plurality of compartments have dimensions suitable for accommodating standard sizes of resealable plastic bags.

3. An attachable insulating icing system consisting essentially of:
   an insulating layer of wetsuit rubber;
   hook and loop fastener straps and strips affixed to an outer surface of the insulating layer;
   a nylon pouch affixed to an inner surface of the insulating layer; and
   removable ice containers placed within the pouch.

4. An attachable insulating icing system comprising:
   an insulating layer of wetsuit rubber;
   hook and loop fastener straps and strips affixed to an outer surface of the insulating layer;
   a pouch of nylon affixed to an inner surface of the insulating layer, the pouch being separated into a plurality of compartments by hook and loop fasteners; and
   a removable ice container placed within the pouch, the ice container being a resealable plastic bag.

* * * * *